United States Patent
Beck et al.

(10) Patent No.: US 7,472,702 B2
(45) Date of Patent: Jan. 6, 2009

(54) METHOD AND DEVICE RESPONSIVE TO DIAPHRAGMATIC ACTIVITY FOR ADJUSTING POSITIVE PRESSURE ASSIST DURING EXPIRATION

(75) Inventors: Jennifer Beck, Toronto (CA); Christer Sinderby, Toronto (CA)

(73) Assignee: Maquet Critical Care AB (SE)

( * ) Notice: Subject to any disclaimer, the term of this patent is extended or adjusted under 35 U.S.C. 154(b) by 622 days.

(21) Appl. No.: 10/808,722

(22) Filed: Mar. 25, 2004

(65) Prior Publication Data

US 2005/0211246 A1   Sep. 29, 2005

(51) Int. Cl.
  *A61M 11/00* (2006.01)
(52) U.S. Cl. .................................. 128/204.23; 600/546
(58) Field of Classification Search ................. 600/546, 600/593, 529, 587, 547; 128/204.23, 204.18, 128/204.26, 204.21
See application file for complete search history.

(56) References Cited

U.S. PATENT DOCUMENTS

| | | | |
|---|---|---|---|
| 5,671,752 A | 9/1997 | Sinderby et al. | |
| 5,820,560 A | 10/1998 | Sinderby et al. | |
| 6,273,088 B1 | 8/2001 | Hillsman | |
| 6,390,091 B1 | 5/2002 | Banner et al. | |
| 6,411,843 B1 * | 6/2002 | Zarychta | 600/546 |
| 6,622,726 B1 | 9/2003 | Du | |
| 6,920,878 B2 * | 7/2005 | Sinderby et al. | 128/204.23 |
| 7,162,296 B2 * | 1/2007 | Leonhardt et al. | 600/547 |

FOREIGN PATENT DOCUMENTS

| WO | WO 99/62580 | * 12/1999 |
|---|---|---|
| WO | 2004/047621 | 6/2004 |

OTHER PUBLICATIONS

International Search Report, International Application No. PCT/CA05/000095, Mailed May 25, 2005, 7 pgs.
Findley, Larry J., et al., "Hypoxemia During Apnea in Normal Subjects: Mechanisms and Impact of Lung Volume," J. Appl. Physiol.; Dec. 1983; 55(6); pp. 1777-1783.
Kosch, Philip C., et al., "Dynamic Maintenance of End-Expiratory Lung Volume in Full-Term Infants," J. Appl. Physiol.; Oct. 1984; 57(4); pp. 1126-1133.
Lopes, J., et al., "Importance of Inspiratory Muscle Tone in Maintenance of FRC in the Newborn," J. Appl. Physiol.; Oct. 1981; 51(4); 830-4.
Mortola, Jacopo P., et al., "Dynamics of Breathing in Infants," J. Appl. Physiol.; May 1982; 52(5); pp. 1209-1215.

* cited by examiner

*Primary Examiner*—Steven O Douglas
(74) *Attorney, Agent, or Firm*—K&L Gates LLP

(57) ABSTRACT

A method and device for controlling positive pressure assist to a patient during expiration, measure a level of electrical activity of a patient's respiration-related muscle during expiration. In response to the measured level of electrical activity, a level of positive pressure assist to the patient during expiration is adjusted in view of minimizing the level of electrical activity of the patient's respiration-related muscle during expiration.

30 Claims, 4 Drawing Sheets

METHOD AND DEVICE RESPONSIVE TO DIAPHRAGMATIC ACTIVITY FOR ADJUSTING POSITIVE PRESSURE ASSIST DURING EXPIRATION

FIELD OF THE INVENTION

The present invention relates to a method and device for controlling positive pressure assist to a patient during expiration in relation to the electrical activity of a respiration-related muscle of the patient during expiration.

More specifically, but not exclusively, the present invention relates to a method and device for adjusting, during mechanical ventilation of a patient, a ventilation feature selected, for example, from the group consisting of: Positive End-Expiratory Pressure (PEEP), Continuous Positive Airway Pressure (CPAP), Biphasic Positive Airway Pressure (BiPAP), and any other mode of mechanical ventilation that provides positive pressure assist to the patient during expiration.

BACKGROUND OF THE INVENTION

PEEP is a standard treatment for the care of patients undergoing mechanical ventilation. PEEP consists of applying a constant positive pressure to the patient's airways during expiration, with the aim of avoiding expiratory lung collapse. Application of PEEP is particularly important during mechanical ventilation of infants demonstrating lower than adequate End-Expiratory Lung Volumes (EELV). The combination of a highly compliant chest wall, and a small caliber of intrathoracic airways predispose infants to closure of the small airways, alveolar collapse at the end of expiration, and thus predispose to hypoxemia [Findley, L. J.; Ries, A. L.; Tisi, M.; Wagner, P. D.; "Hypoxemia During Apnea in Normal Subjects: Mechanisms and Impact of Lung Volume"; J. Appl. Physiol.; December 1983; 55(6); pp 1777-83].

Continuous Positive Airway Pressure (CPAP) is a continuous delivery of positive airway pressure to the patient during both inspiration and expiration, while Biphasic Positive Airway Pressure (BiPAP) is a biphasic delivery of positive airway pressure to the patient.

A variety of different interfaces (nasal prongs, face mask, or endotracheal tube, etc.) are currently used to deliver CPAP to a patient's airways via either continuous or variable gas flow ventilators. CPAP is sometimes also called Continuous Distending Pressure (CDP). The function of CPAP is to keep the patient's airways open.

BiPAP can be described as pressure-controlled ventilation in a system allowing unrestricted spontaneous breathing at any moment of the ventilatory cycle. It can also be described as a CPAP system with a time-cycled change of the level of applied CPAP. BiPAP is not necessarily time-cycled; it can be triggered by the patient. As with a pressure controlled, time-cycled mode, the duration of each phase (T(high), T(low)) as well as the corresponding pressure levels (P(high), P(low)) can be adjusted independently from each other.

Normally, the vagally-mediated Hering-Breuer (H-B) reflexes play a role in the maintenance of an adequate EELV. It is currently believed that, in mammals, phasic stimulation of slowly adapting pulmonary stretch receptors located throughout the tracheobronchial tree and lungs, as would occur with each breath, modulates the frequency of breathing by inhibiting further inspiration during the inspiratory phase or causing prolongation of expiration during the expiratory phase; this is the Hering-Breuer reflex. Tonic stimulation of the same receptors, or other receptors, will also occur with changes in residual lung volume (or Functional Residual Capacity (FRC)) to alter the timing of inspiration relative to expiration in a manner that acts to stabilize the residual lung volume. There may be other reflexes involved, but to date this is the most frequently described reflex. The mechanisms involved with regulating EELV comprise:

1. Braking of Expiratory Flow:
    It has been suggested that changes in a patient's upper airway resistance "brakes" expiration to EELV in order to promote an increase in EELV [Kosch, P. C.; Stark, A. R.; "Dynamic Maintenance of End-Expiratory Lung Volume in Full-Term Infants"; J. Appl. Physiol.; October 1984; 57(4); pp 1126-33]. It has also been claimed that EELV is maintained by post-inspiratory EAdi (Electrical Activity of the diaphragm) [Mortola, J. P.; Fisher, J. T.; Smith, B.; Fox, G.; Weaks, S.; "Dynamics of Breathing in Infants"; J. Appl. Physiol.; May 1982; 52(5); pp 1209-15].

2. Tonic EAdi:
    The article [Lopes, J.; Muller, N. L.; Bryan, M. H.; Bryan, A. C.; "Importance of Inspiratory Muscle Tone in Maintenance of FRC in the Newborn"; J. Appl. Physiol.; October 1981; 51(4); 830-4] points out the contribution of tonic EAdi (persistence of EAdi throughout the entire expiration) in the maintenance of EELV.

3. Respiratory Timing:
    A decrease in FRC reflexly increases Te, which increases EELV by causing intrinsic PEEP. As indicated in the foregoing description, FRC is the Functional Residual Capacity, i.e. the volume of air in the lungs at the end of passive expiration. Te is the neural expiratory time defined as the time between the end of neural inspiration and the beginning of the subsequent neural inspiration.

The expiratory braking mechanism is non-functional in intubated, mechanically ventilated infants, because the endotracheal tube maintains the infant's upper airways patent, albeit the presence of activation of the upper airway muscles. This interferes with the maintenance of EELV in intubated babies; the intubated babies must rely on the remaining two mechanisms ((2) Tonic EAdi (3) Respiratory timing) to maintain their EELV. Externally applied PEEP is almost always used in intubated babies with the intention of maintaining EELV; however, the level of PEEP to be applied is still determined in a more or less arbitrary fashion.

The presence of tonic EAdi in mechanically ventilated infants has been previously demonstrated and quantified [Emeriaud, G.; Beck, J. C.; Tucci, M.; Lacroix, J.; Sinderby, C.; "Diaphragm Electrical Activity during Expiration in Mechanically Ventilated Infants; 2003 ATS Abstract]. The diaphragm remains partially active during expiration, and is characterized by an initial period of post-inspiratory EAdi followed by tonic EAdi. The mean value of this tonic EAdi was 12-14% of the inspiratory Eadi. However, as can be seen in appended FIG. 1, this end-expiratory tonic EAdi is quite variable.

SUMMARY OF THE INVENTION

More specifically, in accordance with the present invention, there is provided a method of controlling positive pressure assist to a patient during expiration, comprising: measuring a level of electrical activity of a patient's respiration-related muscle during expiration; and, in response to the measured level of electrical activity, adjusting a level of positive pressure assist to the patient during expiration in view of minimizing the level of electrical activity of the patient's respiration-related muscle during expiration.

Also in accordance with the present invention, there is provided a device for controlling positive pressure assist to a patient during expiration, comprising: means for measuring a level of electrical activity of a patient's respiration-related muscle during expiration; and means for, in response to the measured level of electrical activity, adjusting a level of positive pressure assist to the patient during expiration in view of minimizing the level of electrical activity of the patient's respiration-related muscle during expiration.

The present invention further relates to a device for controlling positive pressure assist to a patient during expiration, comprising: a detector of a level of electrical activity of a patient's respiration-related muscle during expiration; and a controller of a level of positive pressure assist to the patient during expiration, the controller being supplied with the measured level of electrical activity and controlling the level of positive pressure assist to the patient during expiration in view of minimizing the level of electrical activity of the patient's respiration-related muscle during expiration.

The foregoing and other objects, advantages and features of the present invention will become more apparent upon reading of the following non-restrictive description of illustrative embodiments thereof, given by way of example only with reference to the accompanying drawings.

DETAILED DESCRIPTION OF THE ILLUSTRATIVE EMBODIMENT

The non-restrictive illustrative embodiment of the method and device according to the present invention is concerned with control of positive pressure assist (positive pressure/flow/volume) to a patient during expiration in relation to the level of electrical activity of a patient's respiratory-related muscle. More specifically, the non-restrictive illustrative embodiment of the method and device according to the present invention is concerned with control of a ventilation feature selected from the group consisting of PEEP, CPAP and BiPAP, applied to the patient's airway in relation to an EAdi level during expiration.

Although the non-restrictive illustrative embodiment of the method and device according to the present invention will be described in relation to control of a ventilation feature selected from the group consisting of PEEP, CPAP and BiPAP, these method and device can be applied to any other mode of mechanical ventilation that provides assist to a patient during expiration.

Also, although the preamble of this disclosure and the presently described non-restrictive illustrative embodiment of the method and device according to the present invention often make reference to babies and infants, it should be kept in mind that the method and device according to the invention can be applied as well to patients or subjects of any age, including adults.

The illustrative embodiment of the method and device of the present invention is based upon the principle that application of PEEP, CPAP or BiPAP will increase EELV, which in turn, via the tonic H-B reflex, will alter the tonic EAdi level. For example, when the level of PEEP, CPAP or BiPAP applied is too high, EELV will increase, and the tonic EAdi will be altered. One benefit of the illustrative embodiment of the method and device according to the present invention is that tonic EAdi can be maintained at a level that is not too "stressful" for the patient's diaphragm. Another benefit of the illustrative embodiment of the method and device according to the present invention is that expiratory lung collapse is avoided, in particular during the treatment of infants demonstrating lower than adequate EELV's.

Figure 1:
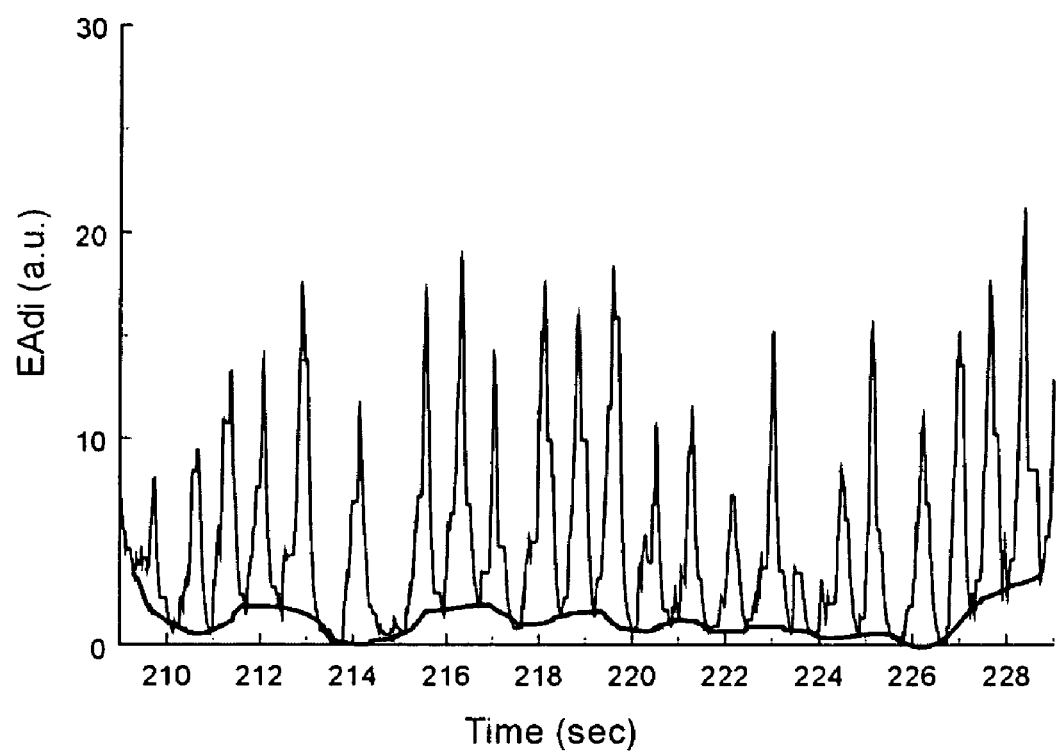
FIG. 1 is a graph showing the level of tonic EAdi of a mechanically ventilated infant during expiration versus time.
Figure 2:
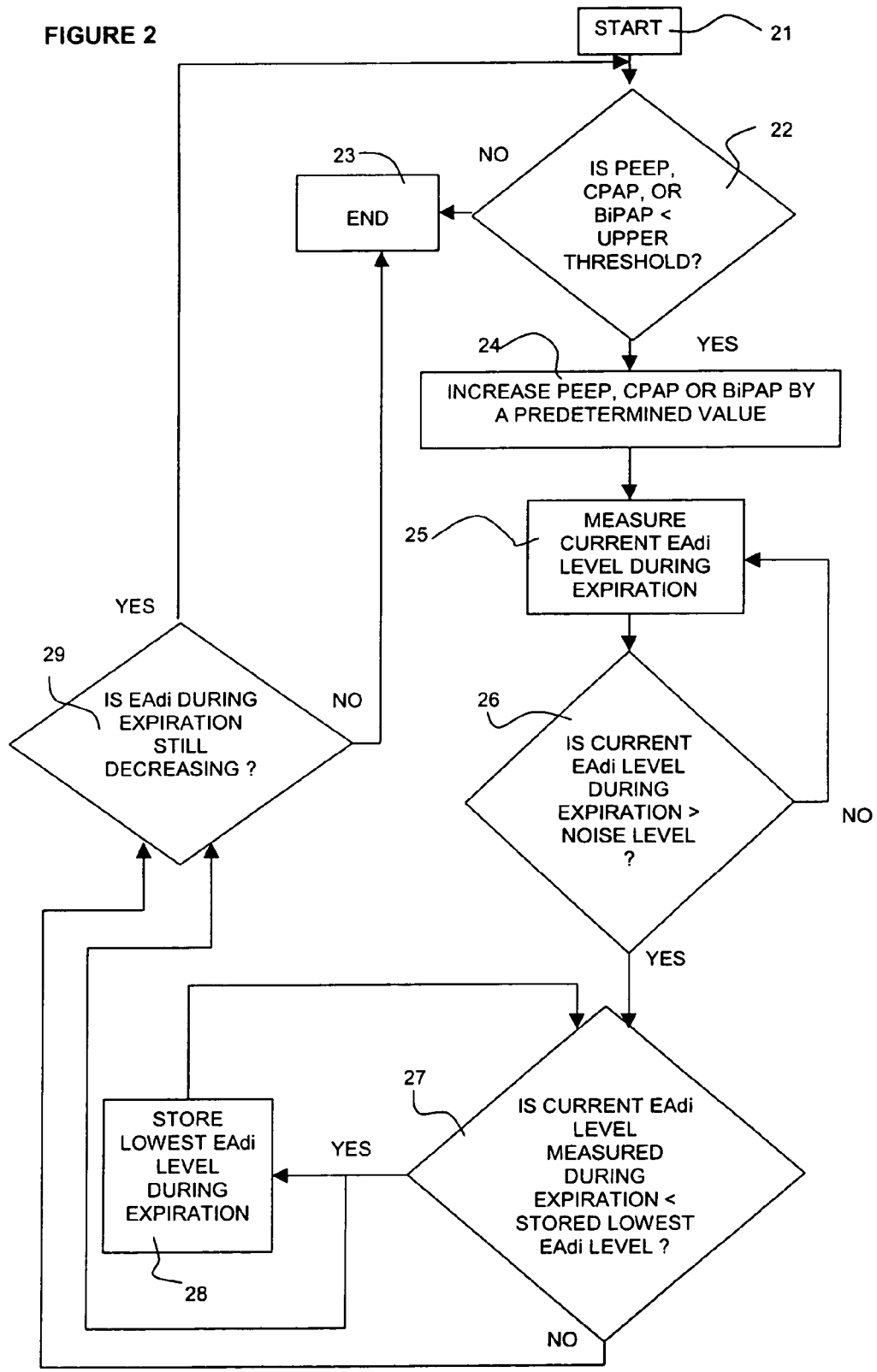
FIG. 2 is a flow chart illustrating the various operations of a non-restrictive illustrative embodiment of the method according to the present invention, for controlling positive pressure assist to a patient during expiration.
Figure 3:
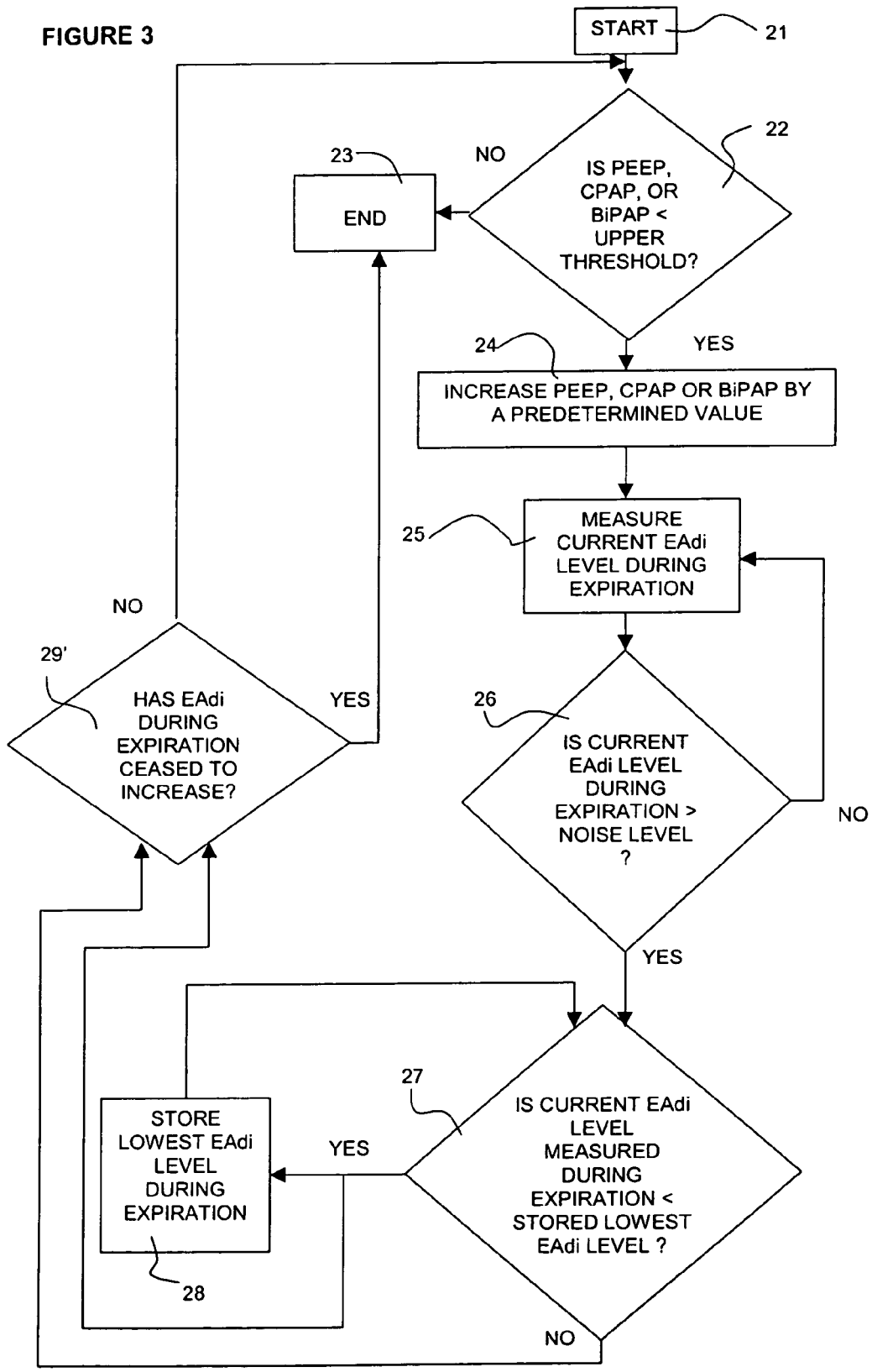
FIG. 3 is a flow chart illustrating the various operations of a non-restrictive illustrative embodiment of the method according to the present invention, for controlling positive pressure assist to a patient during expiration.

Referring now to FIGS. 2 and 3, the non-restrictive illustrative embodiment of the method according to the present invention will now be described.

Operation 21

The method is started.

Operation 22

Since the hemodynamics of the patient, for example blood pressure, could be compromised if PEEP, CPAP or BiPAP during expiration is too high, an upper safety threshold for PEEP, CPAP or BiPAP is imposed by operation 22. This upper safety threshold for PEEP, CPAP or BiPAP during expiration can, for example, be clinically decided upon.

Therefore, operation 22 consists of comparing the current PEEP, CPAP or BiPAP during expiration with this upper safety threshold.

Operation 23

If the comparison performed by operation 22 indicates that the current PEEP, CPAP or BiPAP during expiration is equal to or higher than the safety upper threshold, the method is ended.

Operation 24

If the comparison performed by operation 22 indicates that the current PEEP, CPAP or BiPAP during expiration is lower than the imposed upper safety threshold, the PEEP, CPAP or BiPAP during expiration is increased, for example by a predetermined step.

The PEEP, CPAP or BiPAP can be increased once per patient's expiratory phase. Alternatively, the expiratory phase can be broken down into a plurality of segments and the PEEP, CPAP or BiPAP increased during each of these segments. The various segments can have the same duration or different durations.

Operation 25

A current EAdi level is measured during patient's expiration. For example, the current EAdi level during expiration can be measured by means of the double subtraction technique as described in U.S. Pat. No. 5,671,752 granted to Sinderby et al., on Sep. 30, 1997.

Obviously, the current EAdi level will be measured for each time period for which the PEEP, CPAP or BiPAP is increased, i.e. once per patient's expiratory phase or during each of the above-mentioned segments of the expiratory phase.

To confirm that the electrical activity measured during expiration is actually coming from the diaphragm, the following operations can be performed:

1. Detection of a negative correlation between EAdi signals at some point along a linear array of electrodes used to detect the electrical activity of the patient's diaphragm (see for example the above-mentioned U.S. Pat. No. 5,671,752); and
2. Sum of EAdi signals respectively above and below the diaphragm should be smaller than a difference between these signals.

Operation 26

This operation evaluates whether the current EAdi level measured during expiration is higher than the noise level. This evaluation constitutes an indication that the current measured EAdi level is not just noise but an actual EAdi signal level. Again, this operation will be performed during each time period for which the PEEP, CPAP or BiPAP is increased, i.e. once per patient's expiratory phase or during each of the above-mentioned segments of the expiratory phase.

For example, the EAdi level during expiration can be quantified as an absolute value above the noise level, or a percentage of inspiratory activity.

In this manner, operation 26 ensures that the stored lowest EAdi level during expiration is always higher than the noise level. This stored lowest EAdi level will be described hereinafter.

When the current EAdi level measured during expiration (operation 25) is lower than the noise level as determined by operation 26, the method returns to operation 25 to measure another value for the current EAdi level.

Operation 27

When the current EAdi level measured during expiration (operation 25) is higher than the noise level as determined by operation 26, this current EAdi level is compared to a previously stored (operation 28) lowest EAdi level during expiration to determine whether this current EAdi level is lower than the previously stored lowest EAdi level. Again this comparison is made for each expiratory phase or during each of the above-mentioned segments of the expiratory phase, i.e. for each time period for which PEEP, CPAP or BiPAP is increased.

Operation 28

When comparison between the current EAdi level during expiration and the previously stored lowest EAdi level indicates that the current EAdi level measured during expiration is smaller than the stored lowest EAdi level during expiration, the current EAdi level measured during expiration is stored as the new lowest EAdi level during expiration.

Operations 29 and 29'

The information from operation 27 that (a) the current EAdi level during expiration is higher than the previously stored lowest EAdi level or (b) the current EAdi level during expiration is lower than the previously stored lowest EAdi level is communicated to operation 29 (FIG. 2) or operation 29' (FIG. 3) for each expiratory phase or for each of the above-mentioned segments of the expiratory phase, i.e. for each time period in which PEEP, CPAP or BiPAP is increased.

According to the illustrative embodiment of the method according to the present invention, when the EAdi level during expiration is higher than the noise level (operation 26) or when the EAdi level during expiration increases with time, PEEP, CPAP or BiPAP during expiration will be increased until the EAdi during expiration decreases or ceases to increase.

Operation 29 (FIG. 2)

Therefore, as illustrated in FIG. 2, operation 29 is responsive to the information from operation 27 that (a) the current EAdi level during expiration is higher than the previously stored lowest EAdi level or (b) the current EAdi level during expiration is lower than the previously stored lowest EAdi level to determine whether the EAdi level during expiration decreases in response to increase of PEEP, CPAP or BiPAP during expiration. For example:

when the EAdi level steadily decreases in response to increase of the PEEP, CPAP or BiPAP during expiration, operation 29 will indicate that the EAdi level decreases in response to increasing PEEP, CPAP or BiPAP during expiration; and when the EAdi level has not decreased for a few expiratory phases or a few segments of the expiratory phase, operation 29 will indicate that the EAdi level no longer decreases in response to increasing the PEEP, CPAP or BiPAP during inspiration.

When the decision of operation 29 is that the EAdi level during PEEP, CPAP or BiPAP during expiration decreases in response to increasing PEEP, CPAP or BiPAP, the method returns to operation 22. Otherwise, the method is ended (operation 23).

Operation 29' (FIG. 3)

When the EAdi level during inspiration increases, as illustrated in FIG. 3, operation 29' is responsive to the information from operation 27 that (a) the current EAdi level during expiration is higher than the previously stored lowest EAdi level during expiration or (b) the current EAdi level during expiration is lower than the previously stored lowest EAdi level during expiration to determine whether the EAdi level during expiration has ceased to increase in response to increase of the PEEP, CPAP or BiPAP during expiration. For example:

when the EAdi level continues to increase in response to increase of the PEEP, CPAP or BiPAP during expiration, operation 29' will indicate that the EAdi level during expiration has not yet ceased to increase; and when the EAdi level has stopped to increase for a few expiratory phases or a few segments of the expiratory phase, operation 29' will indicate that the EAdi level during expiration has ceased to increase in response to increasing the PEEP, CPAP or BiPAP during inspiration.

When the decision of operation 29' is that the EAdi level during expiration has not ceased to increase, the method returns to operation 22. When the decision of operation 29' is that the EAdi level during expiration has ceased to increase, the method is ended (operation 23).

Since the patient's status is likely to change over time, verification of the PEEP, CPAP or BiPAP adjustment could also be included in the illustrative embodiment of the method according to the present invention. To verify that the PEEP, CPAP or BiPAP adjustment is appropriate over time, the PEEP, CPAP or BiPAP could be intermittently/periodically reduced to monitor the effect on EAdi. Based on the response, the PEEP, CPAP or BiPAP can be adjusted.

Figure 4:
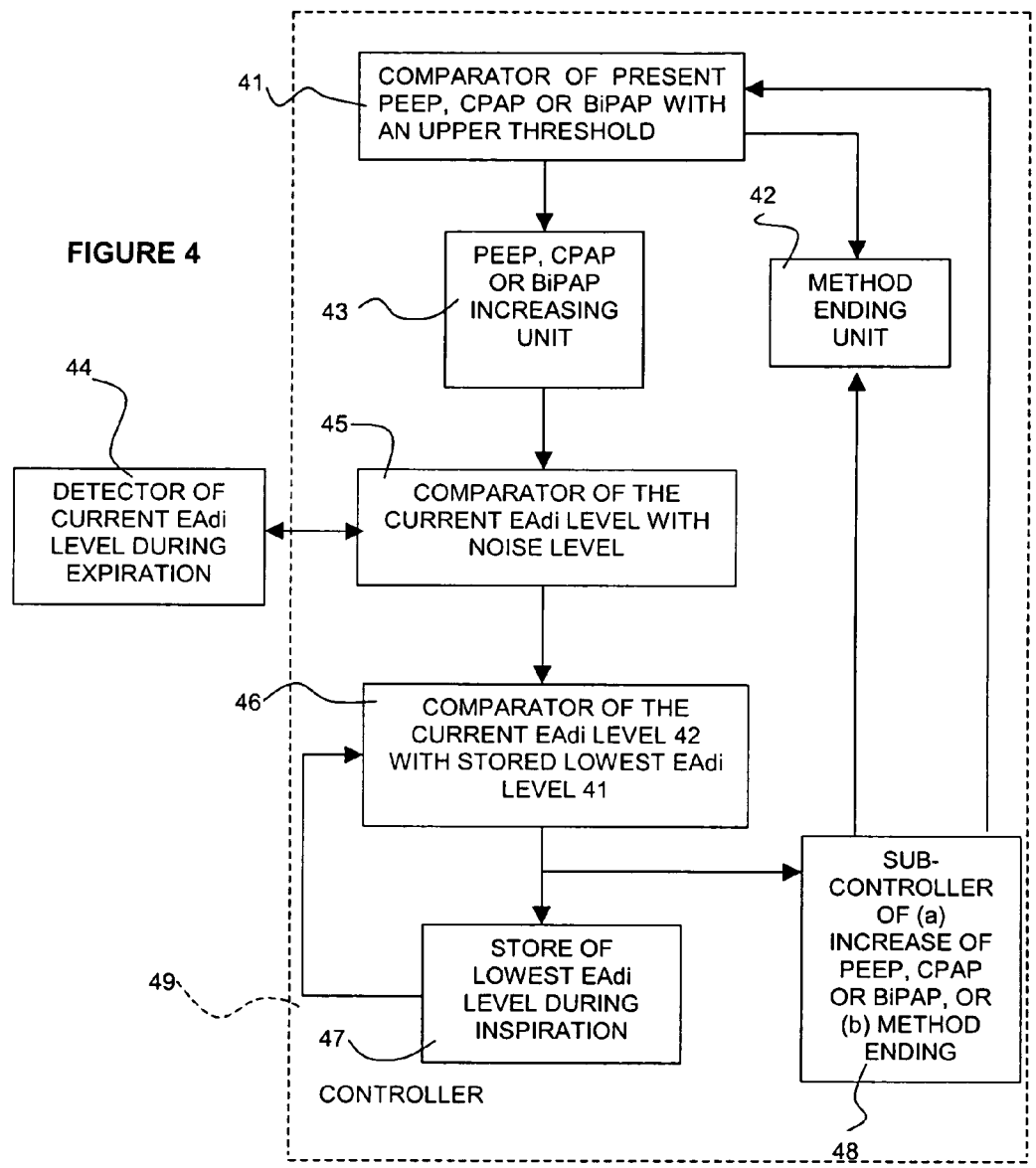
FIG. 4 is a schematic block diagram of a non-restrictive illustrative embodiment of a device according to the present invention, for conducting the method of controlling positive pressure assist to the patient during expiration.

The non-restrictive illustrative embodiment of a device according to the present invention for conducting the method of FIGS. 2 and 3 will now be described with reference to FIG. 4.

This non-restrictive illustrative embodiment of the device according to the present invention comprise a detector 44 of the current EAdi level during inspiration and a controller 49 of the positive pressure assist to a patient during expiration.

In the controller 49, a comparator 41 compares the current PEEP, CPAP or BiPAP during expiration with the upper safety threshold.

When the comparison performed by the comparator 41 indicates that the current PEEP, CPAP or BiPAP during expiration is equal to or higher than the safety upper threshold, the method is ended by a method ending unit 42.

If the comparison performed by the comparator 41 indicates that the current PEEP, CPAP or BiPAP during expiration is lower than the imposed upper safety threshold, a unit 43 increases the PEEP, CPAP or BiPAP during expiration, for example by a predetermined step. Again, the PEEP, CPAP or BiPAP can be increased for each expiratory phase or for each of the above-mentioned segments of the expiratory phase.

A detector 44 measures a current EAdi level during patient's expiration. As indicated in the foregoing description, the current EAdi level during expiration can be measured by means of the double subtraction technique as described in U.S. Pat. No. 5,671,752 granted to Sinderby et al., on Sep. 30, 1997, for each time period for which the PEEP, CPAP or BiPAP is increased, i.e. once per patient's expiratory phase or during each of the above-mentioned segments of the expiratory phase.

A comparator 45 evaluates whether the current EAdi level measured during expiration is higher than the noise level. This evaluation constitutes an indication that the current measured EAdi level is not just noise but an actual EAdi signal level. Again, this operation will be performed during each time period for which the PEEP, CPAP or BiPAP is increased, i.e. once per patient's expiratory phase or during each of the above-mentioned segments of the expiratory phase.

The comparison performed by the comparator 45 ensures that the lowest EAdi level during expiration memorized within the store 47 is always higher than the noise level.

When the current EAdi level measured during expiration by the detector 44 is lower than the noise level as determined by the comparator 45, the detector 44 conducts a new measurement of the current EAdi level.

When the current EAdi level measured during expiration by the detector 44 is higher than the noise level as determined by the comparator 45, another comparator 46 compares the current EAdi level to a lowest EAdi level during expiration previously stored in store 47 to determine whether this current EAdi level is lower than the previously stored lowest EAdi level. Again this comparison is made for each expiratory phase or during each of the above-mentioned segments of the expiratory phase, i.e. for each time period for which PEEP, CPAP or BiPAP is increased.

When comparison between the current EAdi level during expiration and the previously stored lowest EAdi level indicates that the current EAdi level measured during expiration is lower than the stored lowest EAdi level during expiration, the store 37 memorizes the current EAdi level during expiration as the new lowest EAdi level during expiration.

The information from comparator 46 that (a) the current EAdi level during expiration is higher than the previously stored lowest EAdi level or (b) the current EAdi level during expiration is lower than the previously stored lowest EAdi level is communicated to a sub-controller 48 for each expiratory phase or for each of the above-mentioned segments of the expiratory phase, i.e. for each time period in which the PEEP, CPAP or BiPAP is increased.

For example, when the EAdi level steadily decreases in response to increase of the PEEP, CPAP or BiPAP during expiration, the sub-controller 48 will detect that the EAdi level still decreases and will request the comparator 41 and unit 43 to increase the PEEP, CPAP or BiPAP. Also, when the EAdi level has not decreased for a few expiratory phases or a few segments of the expiratory phase, the sub-controller 48 will detect that the EAdi level during expiration no longer decreases and will request the unit 42 to end the method.

According to another alternative, when the EAdi level during inspiration increases, the sub-controller 48 is responsive to the information from the comparator 46 that (a) the current EAdi level during expiration is higher than the previously stored lowest EAdi level or (b) the current EAdi level during expiration is lower than the previously stored lowest EAdi level to determine whether the EAdi level during expiration has ceased to increase in response to increase of the PEEP, CPAP or BiPAP during expiration. For example:

when the EAdi level continues to increase in response to increase of the PEEP, CPAP or BiPAP during expiration, the sub-controller 48 will detect that the EAdi level has not ceased to decrease and will request the comparator 41 and unit 43 to increase the PEEP, CPAP or BiPAP; and when the EAdi level has stopped to increase for a few expiratory phases or a few segments of the expiratory phase, the sub-controller 48 will detect that the EAdi level has ceased to increase in response to increasing the PEEP, CPAP or BiPAP during inspiration and will request the unit 42 to end the method.

Although the present invention has been described hereinabove in connection with illustrative embodiments thereof, these illustrative embodiments can be modified at will, within the scope of the appended claims without departing from the spirit and nature of the subject invention.

What is claimed is:

1. A method of controlling positive pressure assist to a patient during expiration, the method comprising:

measuring a level of electrical activity of a patient's respiration-related muscle during expiration; and adjusting a level of positive pressure assist to the patient during expiration in response to the measured level of electrical activity; wherein adjusting the level of positive pressure assist to the patient during expiration comprises minimizing the level of electrical activity of the patient's respiration-related muscle during expiration; and wherein minimizing the level of electrical activity of the patient's respiration-related muscle during expiration controls stress on the respiration-related muscle while avoiding patient's lung collapse.

2. A method of controlling positive pressure assist to a patient as defined in claim 1, wherein measuring a level of electrical activity of a patient's respiration-related muscle during expiration comprises:

measuring a level of electrical activity of the patient's diaphragm during expiration.

3. A method of controlling positive pressure assist to a patient as defined in claim 1, wherein adjusting a level of positive pressure assist to the patient during expiration comprises:

adjusting a level of a ventilation feature related to a mode of mechanical ventilation providing assist to a patient during expiration.

4. A method of controlling positive pressure assist to a patient as defined in claim 3, comprising:

selecting the ventilation feature from the group consisting of PEEP, CPAP and BiPAP.

5. A method of controlling positive pressure assist to a patient as defined in claim 1, wherein measuring a level of electrical activity of a patient's respiration-related muscle during expiration comprises:

measuring a level of electrical activity of the patient's respiration-related muscle during each patient's expiratory phase.

6. A method of controlling positive pressure assist to a patient as defined in claim 1, wherein measuring a level of electrical activity of a patient's respiration-related muscle during expiration comprises:

dividing a patient's expiratory phase into a plurality of segments; and measuring a level of electrical activity of the patient's respiration-related muscle during each segment of the patient's expiratory phase.

7. A method of controlling positive pressure assist to a patient as defined in claim 3, wherein adjusting a level of positive pressure assist to the patient during expiration comprises:

comparing the level of the ventilation feature to an upper safety threshold; and increasing the level of the ventilation feature by a predetermined step when the comparison indicates that the level of the ventilation feature is lower than the upper safety threshold.

8. A method of controlling positive pressure assist to a patient as defined in claim 7, wherein:

measuring a level of electrical activity of a patient's respiration-related muscle during expiration comprises measuring the level of electrical activity of the patient's respiration-related muscle during expiration after the level of the ventilation feature has been increased by the predetermined step; and adjusting the level of positive pressure assist to the patient during expiration comprises comparing a last measured level of electrical activity of the patient's respiration-related muscle during expiration to a previously stored lowest measured level of electrical activity of the patient's respiration-related muscle during expiration.

9. A method of controlling positive pressure assist to a patient during expiration, the method comprising:

measuring a level of electrical activity of a patient's respiration-related muscle during expiration; and in response to the measured level of electrical activity, adjusting a level of positive pressure assist to the patient during expiration in view of minimizing the level of electrical activity of the patient's respiration-related muscle during expiration;

wherein adjusting the level of positive pressure assist to the patient during expiration comprises:

comparing a last measured level of electrical activity of the patient's respiration-related muscle during expiration to a previously stored lowest measured level of electrical activity of the patient's respiration-related muscle during expiration; and when the comparison between the last measured level of electrical activity and the previously stored lowest measured level of electrical activity indicates that the last measured level of electrical activity is lower than the previously stored lowest measured level of electrical activity, storing the last measured level of electrical activity as the lowest measured level of electrical activity.

10. A method of controlling positive pressure assist to a patient during expiration, the method comprising:

measuring a level of electrical activity of a patient's respiration-related muscle during expiration; and in response to the measured level of electrical activity, adjusting a level of positive pressure assist to the patient during expiration in view of minimizing the level of electrical activity of the patient's respiration-related muscle during expiration;

wherein adjusting the level of positive pressure assist to the patient during expiration comprises:

adjusting a level of a ventilation feature related to a mode of mechanical ventilation providing assist to the patient during expiration;

comparing a last measured level of electrical activity of the patient's respiration-related muscle during expiration to a previously stored lowest measured level of electrical activity of the patient's respiration-related muscle during expiration; and controlling the level of the ventilation feature in relation to the comparison between the last measured level of electrical activity and the previously stored lowest measured level of electrical activity.

11. A method of controlling positive pressure assist to a patient during expiration, the method comprising:

measuring a level of electrical activity of a patient's respiration-related muscle during expiration; and in response to the measured level of electrical activity, adjusting a level of positive pressure assist to the patient during expiration in view of minimizing the level of electrical activity of the patient's respiration-related muscle during expiration;

wherein adjusting the level of positive pressure assist to the patient during expiration comprises:

comparing a last measured level of electrical activity of the patient's respiration-related muscle during expiration to a previously measured lowest level of electrical activity of the patient's respiration-related muscle; and adjusting the level of positive pressure assist to the patient during expiration in relation to the comparison between the last measured level of electrical activity and the previously measured lowest level of electrical activity.

12. A method of controlling positive pressure assist to a patient as defined in claim 11, wherein adjusting the level of positive pressure assist to the patient during expiration comprises:

increasing the level of positive pressure assist to the patient during expiration when the comparison between the last measured electrical activity and the previously measured lowest level of electrical activity indicates that the electrical activity of the patient's respiration-related muscle during expiration decreases.

13. A method of controlling positive pressure assist to a patient as defined in claim 11, wherein adjusting the level of positive pressure assist to the patient during expiration comprises:

increasing the level of positive pressure assist to the patient during expiration when the comparison between the last measured level of electrical activity and the previously measured lowest level of electrical activity indicates that the electrical activity of the patient's respiration-related muscle during expiration has not ceased to increase.

14. A method of controlling positive pressure assist to a patient as defined in claim 11, wherein adjusting a level of positive pressure assist to the patient during expiration comprises:

before comparing the last measured level of electrical activity to the previously stored lowest measured level of electrical activity, determining whether the last measured level of electrical activity is higher than a noise level.

15. A method of controlling positive pressure assist to a patient as defined in claim 3, comprising:

reducing the adjusted level of the ventilation feature;

monitoring the effect of reducing the adjusted level of the ventilation feature on the level of electrical activity of the patient's respiration-related muscle during expiration; and adjusting the level of positive pressure assist to the patient during expiration both (a) in relation to the monitored effect of reducing the adjusted level of the ventilation feature on the level of electrical activity of the patient's respiration-related muscle during expiration and (b) in view of minimizing the level of electrical activity of the patient's respiration-related muscle during expiration.

16. A device for controlling positive pressure assist to a patient during expiration, comprising:
   means for measuring a level of electrical activity of a patient's respiration-related muscle during expiration; and
   means for adjusting a level of positive pressure assist to the patient during expiration in response to the measured level of electrical activity; wherein the means for adjusting the level of positive pressure assist to the patient during expiration comprises means for minimizing the level of electrical activity of the patient's respiration-related muscle during expiration; and wherein minimizing the level of electrical activity of the patient's respiration-related muscle during expiration controls stress on the respiration- related muscle while avoiding patient's lung collapse.

17. A device for controlling positive pressure assist to a patient during expiration, comprising:
   a detector of a level of electrical activity of a patient's respiration-related muscle during expiration; and
   a controller of a level of positive pressure assist to the patient during expiration, the controller being supplied with the detected level of electrical activity and controlling the level of positive pressure assist to the patient during expiration, the controller further minimizing the level of electrical activity of the patient's respiration-related muscle during expiration, wherein minimizing the level of electrical activity of the patient's respiration-related muscle during expiration controls stress on the respiration-related muscle while avoiding patient's lung collapse.

18. A device for controlling positive pressure assist to a patient as defined in claim 17, wherein the detector is:
   a detector of a level of electrical activity of the patient's diaphragm during expiration.

19. A device for controlling positive pressure assist to a patient as defined in claim 17, wherein the controller is:
   a controller of a level of a ventilation feature related to a mode of mechanical ventilation providing assist to the patient during expiration.

20. A device for controlling positive pressure assist to a patient as defined in claim 19, wherein:
   the ventilation feature is selected from the group consisting of PEEP, CPAP and BiPAP.

21. A device for controlling positive pressure assist to a patient as defined in claim 17, wherein the detector detects a level of electrical activity of the patient's respiration-related muscle during each patient's expiratory phase.

22. A device for controlling positive pressure assist to a patient as defined in claim 17, wherein the detector comprises:
   a divider of a patient's expiratory phase into a plurality of segments; and
   a sensor of a level of electrical activity of the patient's respiration-related muscle during each segment of the patient's expiratory phase.

23. A device for controlling positive pressure assist to a patient as defined in claim 19, wherein the controller comprises:
   a first comparator of the level of the ventilation feature to an upper safety threshold; and
   a unit for increasing the level of the ventilation feature by a predetermined step when the comparison conducted by the first comparator indicates that the level of the ventilation feature is lower than the upper safety threshold.

24. A device for controlling positive pressure assist to a patient during expiration, the device comprising:
   a detector of a level of electrical activity of a patient's respiration-related muscle during expiration;
   a controller of a level of positive pressure assist to the patient during expiration, the controller being supplied with the detected level of electrical activity and controlling the level of positive pressure assist to the patient during expiration, the controller further minimizing the level of electrical activity of the patient's respiration-related muscle during expiration, wherein minimizing the level of electrical activity of the patient's respiration-related muscle during expiration controls stress on the respiration-related muscle while avoiding patient's lung collapse;
   wherein the controller comprises:
      a first comparator of a level of a ventilation feature related to a mode of mechanical ventilation providing assist to the patient during expiration to an upper safety threshold; and
      a unit for increasing the level of the ventilation feature by a predetermined step when the comparison conducted by the first comparator indicates that the level of the ventilation feature is lower than the upper safety threshold;
   wherein the detector detects the level of electrical activity of the patient's respiration-related muscle during expiration after the level of the ventilation feature has been increased by the predetermined step; and
   wherein the controller comprises a second comparator of a last detected level of electrical activity of the patient's respiration-related muscle during expiration to a previously stored lowest detected level of electrical activity of the patient's respiration-related muscle during expiration.

25. A device for controlling positive pressure assist to a patient during expiration, the device comprising:
   a detector of a level of electrical activity of a patient's respiration-related muscle during expiration;
   a controller of a level of positive pressure assist to the patient during expiration, the controller being supplied with the detected level of electrical activity and controlling the level of positive pressure assist to the patient during expiration in view of minimizing the level of electrical activity of the patient's respiration-related muscle during expiration;
   a comparator of a last detected level of electrical activity of the patient's respiration-related muscle during expiration to a previously stored lowest detected level of electrical activity of the patient's respiration-related muscle during expiration; and
   a store for storing the last detected level of electrical activity as the lowest detected level of electrical activity when the comparison conducted by the comparator indicates that the last detected level of electrical activity is lower than the previously stored lowest detected level of electrical activity.

26. A device for controlling positive pressure assist to a patient during expiration, the device comprising:
   a detector of a level of electrical activity of a patient's respiration-related muscle during expiration;
   a controller of a level of positive pressure assist to the patient during expiration, the controller being supplied with the detected level of electrical activity and controlling the level of positive pressure assist to the patient during expiration in view of minimizing the level of electrical activity of the patient's respiration-related muscle during expiration;

wherein the controller is a controller of a level of a ventilation feature related to a mode of mechanical ventilation providing assist to the patient during expiration and comprises:

a comparator of a last detected level of electrical activity of the patient's respiration-related muscle during expiration to a previously stored lowest detected level of electrical activity of the patient's respiration-related muscle during expiration; and a sub-controller of the level of the ventilation feature in relation to the comparison conducted by the comparator between the last detected level of electrical activity and the previously stored lowest detected level of electrical activity.

27. A device for controlling positive pressure assist to a patient during expiration, the device comprising:

a detector of a level of electrical activity of a patient's respiration-related muscle during expiration;

a controller of a level of positive pressure assist to the patient during expiration, the controller being supplied with the detected level of electrical activity and controlling the level of positive pressure assist to the patient during expiration in view of minimizing the level of electrical activity of the patient's respiration-related muscle during expiration;

wherein the controller comprises:

a comparator of a last detected level of electrical activity of the patient's respiration-related muscle during expiration to a previously detected lowest level of electrical activity of the patient's respiration-related muscle during expiration; and a sub-controller of the level of positive pressure assist to the patient during expiration in relation to the comparison conducted by the comparator between the last detected level of electrical activity and the previously detected lowest level of electrical activity.

28. A device for controlling positive pressure assist to a patient as defined in claim 27, wherein:

the sub-controller increases the level of positive pressure assist to the patient during expiration when the comparison conducted by the comparator indicates that the electrical activity of the patient's respiration-related muscle during expiration decreases.

29. A device for controlling positive pressure assist to a patient as defined in claim 27, wherein:

the sub-controller increases the level of positive pressure assist to the patient during expiration when the comparison conducted by the comparator indicates that the electrical activity of the patient's respiration-related muscle during expiration has not ceased to increase.

30. A device for controlling positive pressure assist to a patient as defined in claim 27, wherein the controller comprises:

a second comparator for determining whether the last detected level of electrical activity is higher than a noise level before comparing the last detected level of electrical activity to the previously detected lowest level of electrical activity.

* * * * *